(12) United States Patent
Jiménez González et al.

(10) Patent No.: US 12,127,887 B2
(45) Date of Patent: Oct. 29, 2024

(54) METHOD FOR OBTAINING ELASTIC PROPERTIES OF A SOFT SOLID, WHICH USES ACOUSTIC VORTICES

(71) Applicants: CONSEJO SUPERIOR DE INVESTIGACIONES CIENTÍFICAS, Madrid (ES); UNIVERSITAT POLITÈCNICA DE VALÈNCIA, Valencia (ES)

(72) Inventors: Noé Jiménez González, Valencia (ES); José María Benlloch Baviera, Valencia (ES); Francisco Camarena Femenía, Valencia (ES)

(73) Assignees: CONSEJO SUPERIOR DE INVESTIGACIONES CIENTÍFICAS, Madrid (ES); UNIVERSITAT POLITÈCNICA DE VALÈNCIA, Valencia (ES)

( * ) Notice: Subject to any disclaimer, the term of this patent is extended or adjusted under 35 U.S.C. 154(b) by 462 days.

(21) Appl. No.: 17/628,785
(22) PCT Filed: Jul. 14, 2020
(86) PCT No.: PCT/ES2020/070457
§ 371 (c)(1),
(2) Date: Jul. 6, 2022
(87) PCT Pub. No.: WO2021/014040
PCT Pub. Date: Jan. 28, 2021

(65) Prior Publication Data
US 2022/0330919 A1    Oct. 20, 2022

(30) Foreign Application Priority Data
Jul. 22, 2019 (ES) ............................... ES201930675

(51) Int. Cl.
*A61B 8/08* (2006.01)
*A61B 8/00* (2006.01)
(Continued)

(52) U.S. Cl.
CPC ............ *A61B 8/485* (2013.01); *A61B 8/4494* (2013.01); *A61B 8/488* (2013.01); *A61B 8/5223* (2013.01);
(Continued)

(58) Field of Classification Search
CPC .......................... A61B 8/485; G01S 7/52042
See application file for complete search history.

(56) References Cited

U.S. PATENT DOCUMENTS

2018/0168552 A1    6/2018    Shi et al.

FOREIGN PATENT DOCUMENTS

| WO | 2014207605 A1 | 12/2014 |
| WO | 2014207668 A1 | 12/2014 |

(Continued)

OTHER PUBLICATIONS

J.P. Leão-Neto, "Acoustic radiation force and torque exerted on a small viscoelastic particle in an ideal fluid", Journal, 2016, 1-11, vol. 71, Ultrasonics.

(Continued)

*Primary Examiner* — Colin T. Sakamoto
(74) *Attorney, Agent, or Firm* — Hayes Soloway P.C.

(57) ABSTRACT

The present invention relates to a method for obtaining elastic properties of a soft solid by means of quasi-omnidirectional transverse waves generated by a focused ultrasound beam, with a helical phase profile that produces an acoustic vortex that generates a transverse wave front, not only in the direction perpendicular to the ultrasound beam but also in the same direction as the ultrasound beam. The invention also allows control of the transverse wave front generated, which facilitates the carrying out of elastography studies at different frequencies and increases the amplitude of the transverse waves produced, thereby improving the signal-to-noise ratio.

9 Claims, 5 Drawing Sheets

(51) Int. Cl.
  G01S 7/52 (2006.01)
  G01S 15/89 (2006.01)
(52) U.S. Cl.
  CPC ........ A61B 8/5246 (2013.01); G01S 7/52042 (2013.01); G01S 15/8915 (2013.01)

(56) References Cited

FOREIGN PATENT DOCUMENTS

| WO | 2016067072 A1 | 5/2016 |
| WO | 2016102991 A1 | 6/2016 |

OTHER PUBLICATIONS

Daniel H. Cortes, "Continuous Shear Wave Elastography: a New Method to Measure in-vivo Viscoelastic Properties of Tendons", Journal, 2015, 1518-1529, vol. 41, No. 6, Ultrasound in Medicine and Biology.

Fernando Zvietcovich, "Shear wave propagation in viscoelastic media: Validation of an approximate forward model", Journal, 2019, 1-25, vol. 64, No. 2, Physics in Medicine and Biology.

Jean-Luc Gennisson, "Viscoelastic and Anisotropic Mechanical Properties of in Vivo Muscle Tissue Assessed by Supersonic Shear Imaging", Journal, 2010, 789-801, vol. 36, No. 5, Ultrasound in Medicine and Biology.

Brian T. Hefner, "An acoustical helicoidal wave transducer with applications for the alignment of ultrasonic and underwater systems", Journal, 1999, 3313-3316, vol. 106, No. 6, Journal of the Acoustical Society of America.

Noe Jimenez, "Formation of high-order acoustic Bessel beams by spiral diffraction gratings", 2016, Journal, 1-9, vol. 94, Physical Review.

J. Ophir, "Elastography: A Quantitative Method for Imaging the Elasticity of Biological Tissues", Journal, 1991, 111-134, vol. 13, Ultrasonic Imaging.

Jeremy Bercoff, "Supersonic Shear Imaging: A New Technique for Soft Tissue Elasticity Mapping", Journal, 2004, 396-409, vol. 51, No. 4, IEEE Transactions on Ultrasonics, Ferroelectrics, and Frequency Control.

Robert M. Lerner, "Sono-Elasticity: Medical Elasticity Images Derived From Ultrasound Signals in Mechanically Vibrated Targets", Article, 1998, 317-327, Acoustical Imaging.

Caroline Maleke, "Single-Element Focused Ultrasound Transducer Method for Harmonic Motion Imaging", Journal, 2006, 144-158, vol. 28, Ultrasonic Imaging.

Armen P. Sarvazyan, "Shear Wave Elasticity Imaging: a New Ultrasonic Technology of Medical Diagnostics", Journal, 1998, 1419-1435, vol. 24, No. 9, Ultrasound in Medicine and Biology.

Kathryn R. Nightingale, "On the feasibility of remote palpation using acoustic radiation force", Journal, 2001, 625-634, vol. 110, No. 1, Journal of the Acoustical Society of America.

Noe Jimenez, "Sharp acoustic vortex focusing by Fresnel-spiral zone plates", Journal, 2018, 1-6, vol. 112, Applied Physics Letters.

METHOD FOR OBTAINING ELASTIC PROPERTIES OF A SOFT SOLID, WHICH USES ACOUSTIC VORTICES

CROSS-REFERENCE TO RELATED APPLICATIONS AND PRIORITY

This patent application claims priority from PCT Application No. PCT/ES2020/070457 filed Jul. 14, 2020, which claims priority from Spanish Patent Application No. P201930675 filed Jul. 22, 2019. Each of these patent applications are herein incorporated by reference in their entirety.

OBJECT OF THE INVENTION

The present invention relates to a method for obtaining elastic properties of a soft solid by means of quasi-omnidirectional transverse waves generated by a focused vortex ultrasound beam.

BACKGROUND OF THE INVENTION

Elastography imaging is a medical imaging modality that allows the elastic properties of soft tissues to be evaluated. These properties make it possible to detect changes in the stiffness of the tissues associated with underlying pathologies.

Elastography methods propose estimating the elastic properties of tissues by measuring the deformations that are produced when certain external mechanical stress is applied to them.

On the one hand, in quasi-static methods the tissue is compressed externally in a manner analogous to palpation, or by externally applying oscillatory compression on the tissue.

By measuring the amplitude of the deformations produced, an image of the relative stiffness of the tissue is obtained, as proposed in the Sonoelasticity Imaging technique that is featured in the document *Sono-elasticity imaging* by Lerner, R. M.; Parker, K. J. Kessler, L. W., ed. Acoustic imaging. New York: Plenum Co, 317-327. (1988). Said document discusses the use of Doppler imaging techniques to measure the movements of the tissue that is subjected to an external low-frequency vibrator. These movements appear in the form of transverse waves and can be used to obtain information on the elasticity of biological tissues.

Other methods, such as compression elastography described in *Elastography: a quantitative method for imaging the elasticity of biological tissues* by Ophir, J., Cespedes, I., Ponnekanti, H., Yazdi, Y., & Li, X.; Ultrasonic imaging, 13(2), 111-134 (1991), use mechanical compression to take two ultrasound images in B-scan mode. The first is taken as a reference and the second is obtained after applying mechanical compression using the same ultrasound probe. Using cross-correlation techniques, an image of the deformations produced, which provide an image of the elasticity of the medium, is obtained.

The drawback of the previous methods is that the distribution of stresses is not uniform and depends on the geometry of the medium, unknown a priori, so they only provide a qualitative image of the elasticity. Therefore, these quasi-static methods do not allow the elastic properties of tissues to be quantitatively evaluated.

A second generation of methods are those that use the acoustic radiation force produced by a focused ultrasound beam as a mechanism to generate the stress field, wherein the transfer of momentum from the wave to the tissue is due to absorption and reflection on the non-homogeneous areas thereof.

These methods can provide a quantitative image of the elasticity since the deformation of the tissue is carried out by applying stress inside the tissue and said stress is, in principle, known. In general, a primary ultrasound beam is used to produce a deformation in the tissue, whereas a secondary ultrasound beam in pulse-echo mode is used to acquire a set of successive images in B-scan mode.

Using cross-correlation, with which the different images are compared, the deformations produced inside the tissue can be detected. Typically, such movements are a few micrometres in amplitude. In this way, the elastic parameters of the tissue can be calculated by measuring the deformations produced in the tissue when the applied radiation force is known.

Different modalities have been developed using these concepts such as Acoustic Radiation Force Impulse imaging (ARFI), from the document *On the feasibility of remote palpation using acoustic radiation force* by Kathryn R. Rightingale, Mark L. Palmeri, Roger W. Nightingale, and Gregg E. Trahey, J.; *Acoust. Soc. Am.* 110 (1), of July 2001, wherein a technique capable of obtaining images in the mechanical variations of tissues is proposed. The technique uses a radiation force in the axial direction (linear components), and studies the movements in the local area of the focus.

Another example is amplitude-modulated Harmonic Motion Imaging (HMI), from the document *Single-Element Focused Ultrasound Transducer Method for Harmonic Motion Imaging* by Caroline Maleke, Mathieu Pernot and Elisa E. Konofagou; *Ultrasound Imaging* 28, 144-158 (2006), wherein the use of a focused transducer that is excited with a low frequency modulated amplitude is proposed to exert a thrust on the tissue located at the focus thereof. This document starts with a beam that generates a linear, and therefore not helical, thrust.

Other modalities use the shear (or transverse) waves that are generated after the transient application of the primary ultrasound beam. Since shear waves propagate through human tissues at a slow speed (about 1-10 m/s), the deformations produced by the same can be measured by a secondary ultrasound beam.

In this way, by measuring the local propagation speed of the transverse waves, a map of the elastic shear modulus of the medium is obtained, since the propagation speed of the transverse waves is directly determined by the stiffness of the tissues.

An example of these techniques is Shear Wave Elastography Imaging (SWEI), from the document *Shear wave elasticity imaging: a new ultrasonic technology of medical diagnostics* by Sarvazyan, A. P., Rudenko, O. V., Swanson, S. D., Fowlkes, J. B., & Emelianov, S. Y. *Ultrasound in medicine & biology*, 24(9), 1419-1435 (1998), showing a technique to determine the elastic properties of a tissue based on the use of acoustic radiation force to excite it. As in previous techniques, the acoustic radiation force is exerted in the axial direction, but in this case a spatial excitation pattern is defined, i.e., the tissue is excited at different points.

Moreover, Supersonic shear imaging (SSI) is featured in the document *Supersonic Shear Imaging: A New Technique for Soft Tissue Elasticity Mapping* by Jéremy Bercoff, Mickäel Tanter, and Mathias Fink; *IEEE transactions on ultrasonics, ferroelectrics, and frequency control*, vol. 51, no. 4, April 2004. This document proposes a new technique for generating transverse waves in biological tissue.

The technique consists of using the radiation force exerted by an ultrasound beam that is focused on different points of the tissue at a speed greater than the propagation speed of the transverse waves generated in the tissue. This generates a Mach cone with transverse waves of greater amplitude, due to the constructive interference that is generated in the wave fronts.

In all the aforementioned techniques, the transverse waves are generated in the direction perpendicular to the primary ultrasound beam. In this way, the area on the axis of the primary beam is left unscanned since transverse waves are not generated in that direction. Since a focused ultrasound beam that only carries linear momentum is used in these techniques, the stresses produced are only produced in the direction of the axial beam.

There are other types of ultrasound beams that, in addition to carrying linear momentum, also carry angular momentum. These beams are vortex beams (or acoustic vortices). An example of a device capable of producing said vortex beams is that described in the document by Hefner, B. T., & Marston, P. L. (1999), *An acoustical helicoidal wave transducer with applications for the alignment of ultrasonic and underwater systems; The Journal of the Acoustical Society of America,* 106(6), 3313-3316. In this work, two methods are presented, one active and the other passive, to generate acoustic vortices. The active method uses four piezoelectric transducers fed with different phase and the passive method uses a single transducer with a helical surface.

Other methods include spiral grids, such as those described in the documents *Sharp acoustic vortex focusing by Fresnel-spiral zone plates* by Jiménez, N., Romero-García, V., García-Raffi, L. M., Camarena, F., & Staliunas, K. Applied Physics Letters, 112(20), 204101. (2018) and in the document *Formation of high-order acoustic Bessel beams by spiral diffraction gratings* by Jiménez, N., Picó, R., Sánchez-Morcillo, V., Romero-García, V., García-Raffi, L. M., & Staliunas, K.; Physical Review E, 94(5), 053004. (2016).

However, the radiation force applied in all currently available elastography techniques has the direction of the generated excitation beam, so that the radiation pattern of the transverse waves is limited, the excitation frequency cannot be defined and the amplitude of the generated transverse waves is low.

DESCRIPTION OF THE INVENTION

The present invention provides an improvement with respect to prior methods by broadening the radiation pattern of the generated transverse waves, allowing the excitation frequency of the transverse waves to be defined, and increasing the amplitude of the generated transverse waves.

The invention is based on the use of a vortex ultrasound beam that produces a torsional stress field, which generates a transverse wave front inside a soft solid, and which is used to determine a series of elastic properties of said soft solid, which is preferably a tissue, such as liver or prostate, from a patient to be diagnosed.

Specifically, with the present method, a quasi-omnidirectional transverse wave front is generated from a focused ultrasound beam, with a helical phase profile, i.e., an acoustic vortex, the wave front propagating through the soft solid, so that all areas of interest around the ultrasound beam are covered.

This offers several significant advantages with respect to the other elastography imaging techniques of the state of the art. In the first place, current techniques are only capable of generating the wave front in the direction perpendicular to the axis of the focused ultrasound beam, such that they do not propagate in the direction axial to the focus, which is why it is very difficult to extract the elastic parameters from that area.

Secondly, the amplitude of the generated waves is greater for one same acoustic intensity, which allows the signal-to-noise ratio of the image to be improved and the amplitude level of the beam to be reduced, thus reducing unwanted effects such as the increase in temperature produced by the primary beam.

Thirdly, if the direction of angular rotation of the acoustic vortex is controlled and varied as a function of time, it is possible to control the frequency of the transverse waves produced and therefore the wavelength thereof inside the tissue. Finally, the control of the direction of rotation allows the polarisation of the transverse waves to be controlled, allowing the anisotropy of the tissues to be evaluated, as occurs, for example, in fibrous tissues.

Preferably, this method is used to obtain the elastic properties of a patient's tissue. The information obtained on the elastic properties of the tissue is used to make a medical diagnosis and detect possible anomalies in said tissue, which may be the consequence of cancer or some other type of injury, and which are accompanied by changes in the elastic properties of the tissues.

The first step of the method consists of applying a pulsed or amplitude-modulated signal to an ultrasound transducer that has a surface intended to make contact with the tissue to be studied. This signal is comprised in the ultrasound range (with a carrier frequency between 0.2 MHz and 20 MHz). Specifically, it would be a sinusoidal signal with a modulation frequency equal to that of the transverse wave front to be generated.

Once the signal is applied to the ultrasound transducer, a focused vortex ultrasound beam is generated, which in turn generates a quasi-omnidirectional transverse wave front that is transmitted through the soft solid.

The ultrasound transducer used can be of two different types, and depending on which one is used, the strategy to generate the acoustic vortex will be different.

Firstly, a single element transducer can be used, comprising a holographic lens. Said lens is intended to be positioned on the surface $(x_0, y_0)$ of the ultrasound transducer. The wave front is characterised in that it has a complex amplitude $A(x_0, y_0)$, which is modified by the lens, such that it is adjusted to that of a focused acoustic vortex. The phase is given by the equation:

$$A(x_0, y_0) = \exp(-ik_0\sqrt{x_0^2+y_0^2+F^2})\exp(-im\tan^{-1}(y_0, x_0)) \quad \text{(Equation 1)}$$

wherein $A(x_0, y_0)$ is the complex amplitude along the surface of the ultrasound transducer given by $x_0, y_0$. The wave number is given by $k_0 = 2\pi f/c_0$, wherein f is the carrier frequency and $c_0$ is the speed of sound in the soft solid. F is the focal length of the lens and m the topological charge of the vortex, which is normally an integer. Depending on the sign of m, the vortex rotates clockwise or anticlockwise.

The lens, therefore, must be capable of producing the phase profile $A(x_0, y_0)$. To do this, one strategy is to divide the lens into pixels and define a height for each pixel as $h(x_0, y_0)$ so that it fulfills:

$$A(x_0, y_0) = \frac{2Ze^{-ik_0[d-h(x_0)]}}{2Z\cos[k_L h(x_0)] + i(Z^2+1)\sin[k_L h(x_0)]},$$ (Equation 2)

$Z=\rho_L c_L$ being the impedance of the lens, wherein $\rho_L$ is the density of the lens and $c_L$ the propagation speed of ultrasound in the lens. $k_L=2\pi f/c_L$, and d is an arbitrary distance that coincides with the surface plane of the ultrasound transducer. Obtaining the heights $h(x_0, y_0)$ as a function of $A(x_0, y_0)$ is carried out using numerical inversion of equation 2.

Secondly, a multi-element (or phased-array) ultrasound transducer can be used. In the event that the array is flat, each element of the transducer will adjust to an amplitude given by |A|, and a phase given by $\tan^{-1}(\text{Im}(A)/\text{Re}(A))$, wherein A is given by Equation 2, Re(•) indicates the real portion and Im(•) the imaginary portion of the complex value. The coordinates $x_0$ and $y_0$ are given by the spatial positions in Cartesian coordinates of each element of the ultrasound transducer.

In the event that the array is a geometric focusing array, as in the case of a multi-element wherein each element is arranged on the surface of a sphere of radius F, the same method is applied as in the previous case, but the expression to use is:

$$A(x_0,y_0)=\exp(-im\tan^{-1}(x_0,y_0)).$$ (Equation 3)

In other words, it is a phase profile that linearly depends on the polar angle occupied by each element of the phased-array.

Therefore, regardless of the type of ultrasound transducer used, the emitted ultrasound beam has an acoustic intensity that rotates with respect to the angular coordinate, and transfers to the soft solid both an amount of linear momentum in the direction of the ultrasound beam and an angular momentum in the form of a torus around the ultrasound beam.

In particular, a force field is transmitted to the soft solid that can be calculated as:

$$F(x, y, z) = i\frac{\alpha(\omega)}{2\omega\rho_0 c_0}(P\nabla P^* - P^*\nabla P)$$ (Equation 4)

F being the force vector field, $\alpha(\omega)$ the acoustic absorption of the soft solid, $\omega=2\pi f$ the angular frequency, $\rho_0$ the density, $c_0$ the speed of ultrasound longitudinal waves, P the ultrasound pressure field, and P* the complex conjugate thereof.

In view of the previous force field, it is verified that when the ultrasound field is of the vortex type, a force that is of the torque or torsional type is produced in the soft solid, with a small axial component. Since the soft solid absorbs a large part of the energy of the focused ultrasound beam, the transfer of angular momentum in the form of torque to the soft solid causes a transient deformation thereof, curling it.

In this way, the transverse wave front is generated which propagates not only in the direction perpendicular to the ultrasound beam, but also in the same direction as the ultrasound beam, i.e., a quasi-omnidirectional wave front.

Another advantage offered by the present invention is that by being able to control the parameters that define the ultrasound beam, the polarisation of the wave front that is generated inside the soft solid can be controlled. Specifically, by controlling the sign of the topological charge of the ultrasound beam, the direction of rotation of the stress produced (clockwise/anticlockwise) can be controlled.

As indicated, the topological charge will preferably be equal to one, although if it becomes greater than one, wider force fields with a greater torque are generated.

By controlling the direction of rotation, periodically alternating between one and the other, the waves are excited in both positive and negative cycles, which manages to induce positive and negative deformation cycles in the soft solid, increasing the amplitude of the generated wave front and, therefore, the robustness and sensitivity of the technique. In this way, there is no need to wait for the soft solid to relax before pushing it back and continuously generating waves.

In the event that the ultrasound transducer is a single element, there are different strategies that allow the sign of the topological charge to be controlled.

The first consists of using a lens designed to work with a topological charge at one emission frequency and with another topological charge of the opposite sign at another frequency, to alternate between the two.

The second strategy consists of using two ultrasound transducers, positioned as two concentric rings, each having a different lens, as well as a different topological charge, of opposite signs, and alternating the emission of one and the other.

In the event of a multiple element ultrasound transducer, the control of the sign of the topological charge is simpler, since it is only necessary to angularly revert the phase of the elements of the array, i.e., by reverting the sign of the parameter m in Equation 1 or in Equation 3, respectively.

Therefore, control of the frequency and direction of rotation of the ultrasound beam allows the generated transverse wave front to be controlled, which facilitates the performance of elastography studies at different frequencies.

The next step of the method, once the transverse wave front has been generated, consists of acquiring radiofrequency signals that are reflected by the soft solid at different instants in time, while said wave front is propagated. To do this, a second ultrasound medical imaging transducer can be used, in pulse-echo mode. This secondary transducer is used to obtain a series of ultrasound images at different instants in time taken after or during the activation of the primary transducer.

Once the series of images has been obtained, the next step of the method consists of calculating the deformations using cross-correlation methods or Doppler techniques between the different images. This provides an image of the deformations produced in the tissue as the transverse waves pass through.

From the images of the deformations, using standard tracking techniques, the propagation speed of the transverse wave front is calculated.

Finally, from the speeds, the transverse or shear modulus of elasticity is obtained, which for an elastic medium can be obtained from the equation:

$$v = \sqrt{\frac{G}{\rho}}$$ (Equation 5)

G being the transverse or shear modulus of elasticity and p the density of the soft solid.

The density changes very little with respect to the variation suffered by the transverse modulus of elasticity of the soft solid, such that a difference in speed is fundamentally due to a variation in the transverse modulus of elasticity thereof and, therefore, to some type of alteration in the soft solid analysed.

Finally, from the transverse elastic modulus obtained at different points of the tissue, elastography images are obtained that are used to make a medical diagnosis.

DESCRIPTION OF THE DRAWINGS

To complement the description that is being made and for the purpose of helping to better understand the features of the invention according to a preferred practical exemplary embodiment thereof, a set of drawings is attached as an integral part of said description in which the following is depicted in an illustrative and non-limiting manner.

PREFERRED EMBODIMENT OF THE INVENTION

In view of the figures described above, a non-limiting exemplary embodiment of the method for obtaining elastic properties of a soft solid, object of this invention, can be observed.

Figure 1:
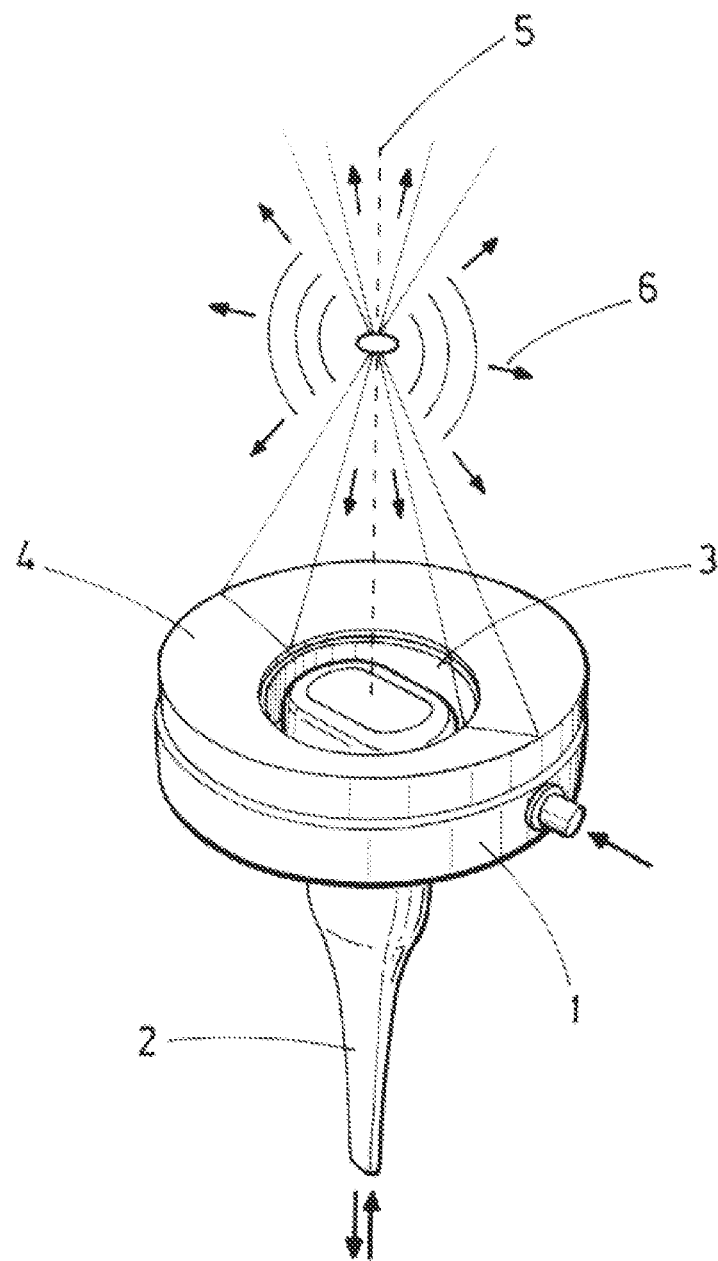
FIG. 1 shows a diagram of the primary and secondary ultrasound transducers used by the method.
Figure 2:
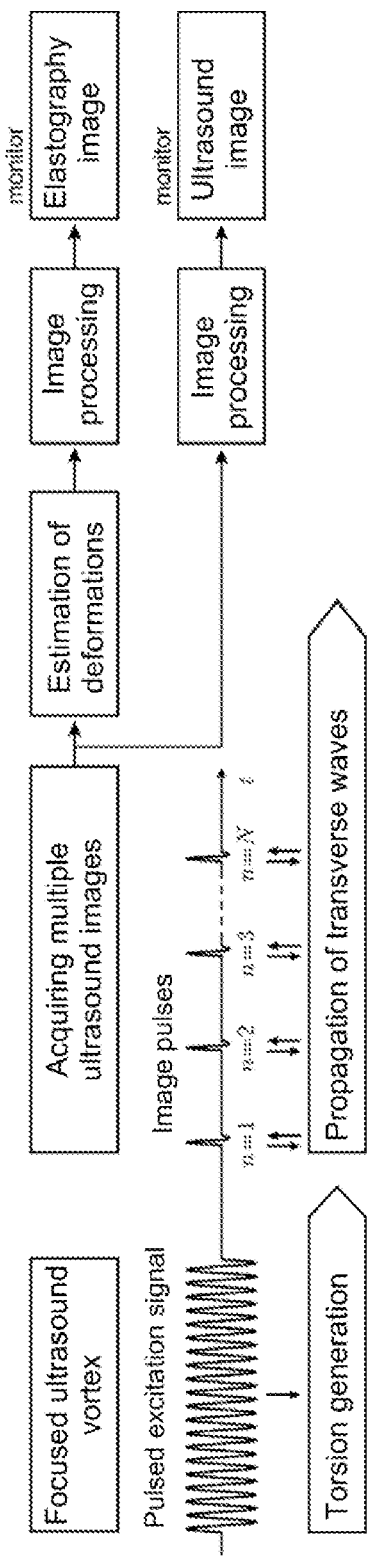
FIG. 2 shows a block diagram of the process wherein a possible sequence to follow is shown.

The first step of the method, a block diagram of which is shown in FIG. 2, consists of applying a pulsed or modulated frequency signal, with a carrier frequency of around 1 MHz, comprised in the ultrasound range, and a modulator frequency in the range from 1 Hz to 1000 Hz, to an ultrasound transducer (1), like the one in FIG. 1, comprising a surface intended to make contact with a soft solid.

Once the signal is applied to the ultrasound transducer (1), a focused ultrasound beam (5) is generated, with a helical phase profile, i.e., an acoustic vortex, and which generates a quasi-omnidirectional transverse wave front (6) that is transmitted through the soft solid. The frequency of the wave front (6) is equal to the modulation frequency of the pulsed signal applied to the ultrasound transducer (1).

The focused vortex ultrasound beam (5) is generated by means of the ultrasound transducer (1) which is multi-element (or phased-array), the array being a geometric focusing array. To do this, each element of the ultrasound transducer (1) is adjusted to an amplitude given by:

$$|A(x_0, y_0)| = \exp(-im \tan^{-1}(x_0, y_0)), \quad \text{(Equation 6)}$$

i.e., a phase profile that linearly depends on the polar angle occupied by each element of the ultrasound transducer (1).

Therefore, the emitted ultrasound beam (5) has an acoustic intensity that rotates with respect to the angular coordinate, which transfers to the soft solid both an amount of linear momentum in the direction of the ultrasound beam and an angular momentum in the form of a torus around the ultrasound beam (5).

Figure 3:
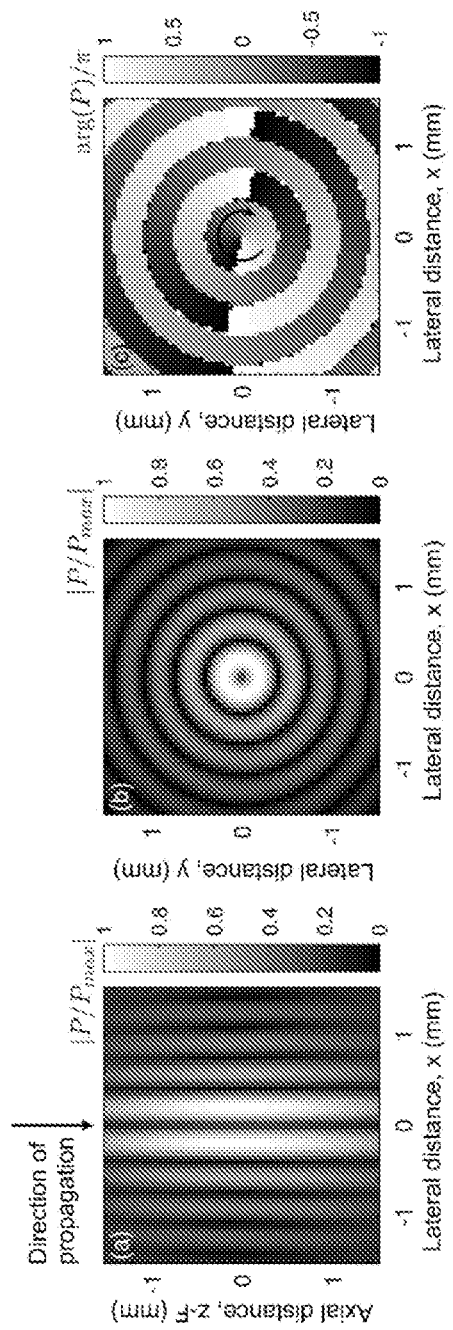
FIG. 3 shows the acoustic field generated by the ultrasound transducer.

FIG. 3 shows the acoustic field generated by the ultrasound transducer (1). Image a) represents the magnitude of the field in the sagittal plane in the direction of propagation y=0. Image b) represents the magnitude of the field in the transverse plane, over the focal length z=F. Image c) represents the phase of the field in the transverse plane, over the focal length z=F.

FIG. 3 shows how a phase singularity is produced on the axis that gives rise to an acoustic vortex. The phase also rotates around the focus an integer number of times.

The transfer of linear momentum generates a force field in the soft solid that can be calculated as:

$$F(x, y, z) = i\frac{\alpha(\omega)}{2\omega\rho_0 c_0}(P\nabla P^* - P^*\nabla P), \quad \text{(Equation 7)}$$

F being the force vector field, $\alpha(\omega)$ the absorption of the soft solid, $\omega$ the angular frequency, $\rho_0$ the density, $c_0$ the speed of front transverse waves, P the pressure field produced, and $P^*$ the complex conjugate thereof.

Figure 4:
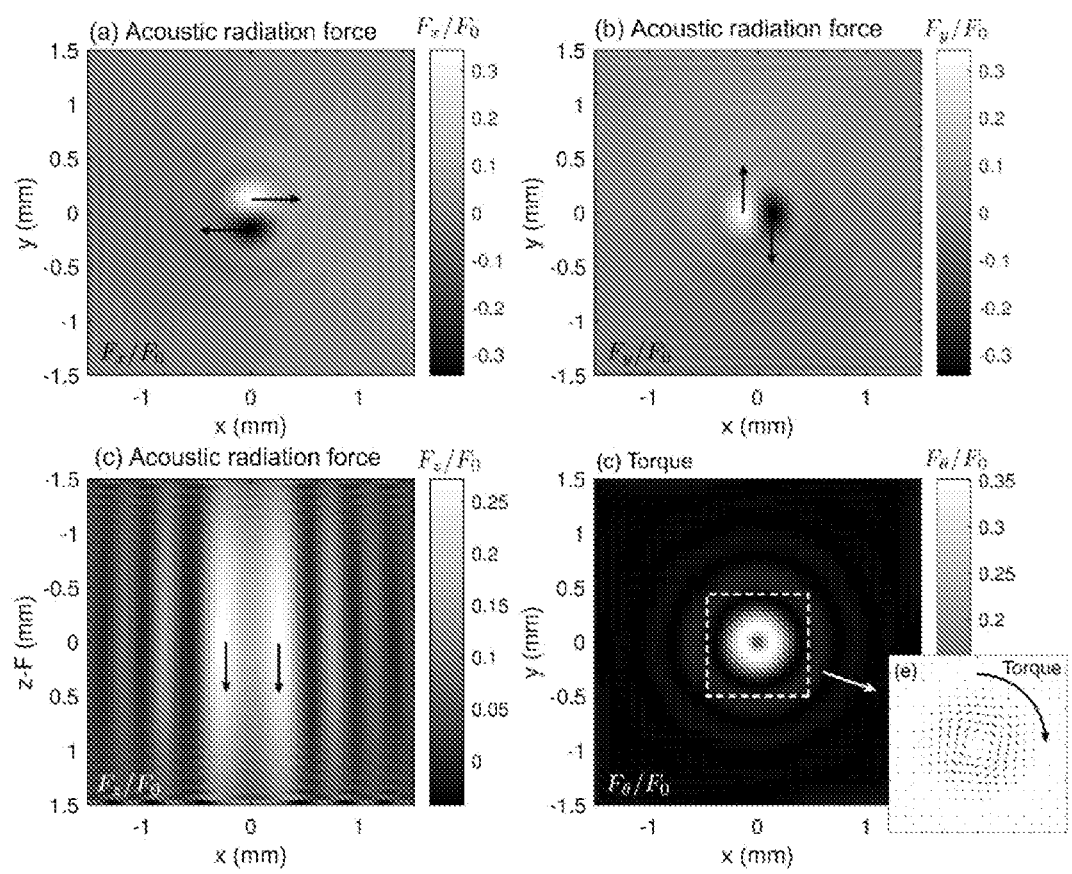
FIG. 4 shows the radiation acoustic force field generated on the soft solid.

This force field is shown in FIG. 4. Graph a) shows a representation in the transverse plane of the force component in the direction x, calculated at z=F. Graph b) is the representation in the transverse plane of the force component in the direction y, calculated at z=F. Graph c) is a representation in the sagittal plane of the force component in the direction z, calculated at y=0. Graph d) is the representation in the transverse plane of the force torque component, calculated at z=F. Subgraph e) is the representation of the vector field.

From the previous force field, a force is produced in the soft solid that is of the torque type, with a small axial component. Since the soft solid absorbs a large part of the energy of the ultrasound beam (5), the transfer of angular momentum in the form of torque to the soft solid causes a transient deformation thereof, curling it.

The next step of the method consists of acquiring radiofrequency signals that are reflected by the soft solid at different instants in time, a process that is repeated while the transverse wave front (6) is propagated. To do this, a second ultrasound medical imaging transducer (2) is used, in pulse-echo mode.

Figure 5:
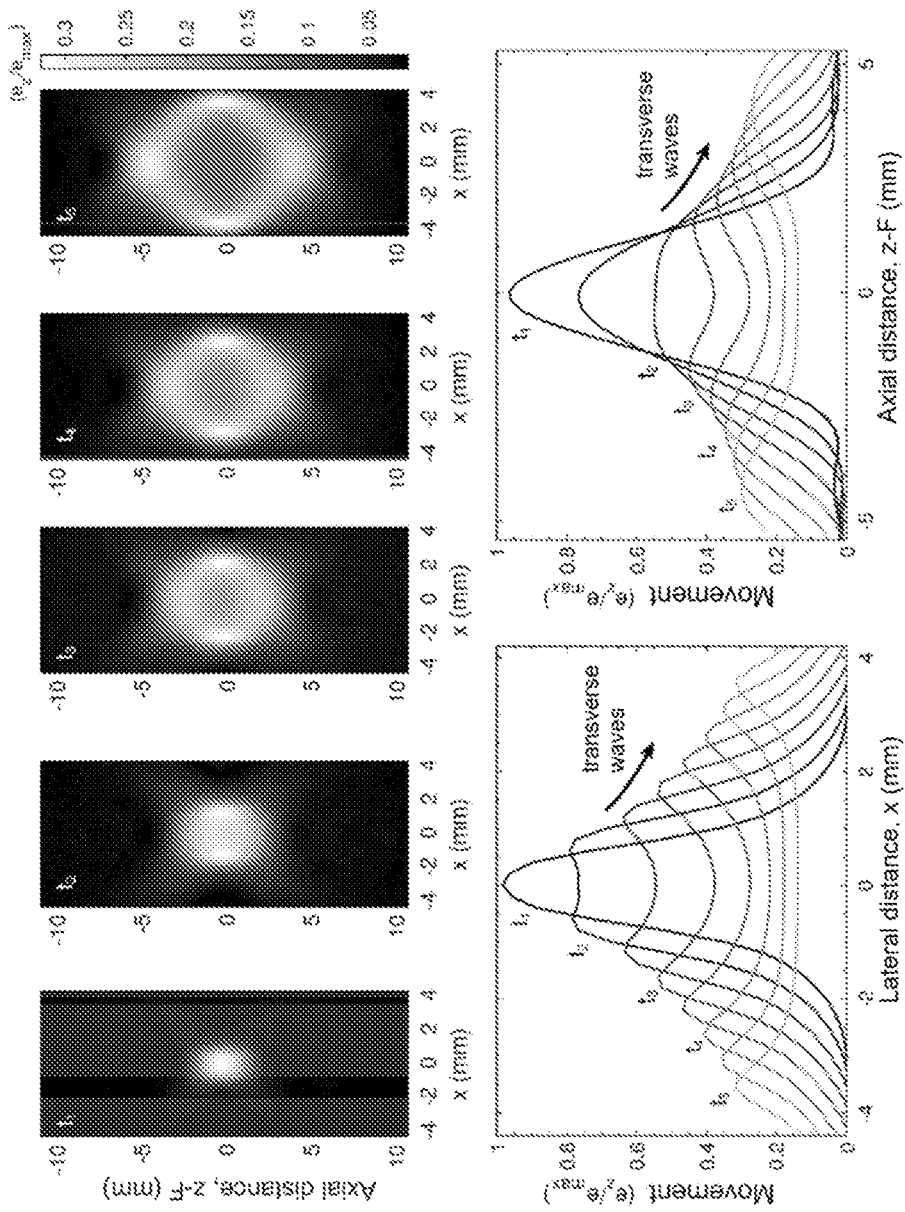
FIG. 5 shows the movement of the soft solid in the direction z at different instants in time.

Once the signals have been obtained, the deformations produced are calculated as a function of time, based on the amplitude of the transverse movements suffered by the soft solid, using cross-correlation or Doppler techniques. These deformations can be observed in the graphs of FIG. 5, wherein the movement of the tissue in the direction z is reflected, at different instants in time, from t=0.6 ms to t=2.4 ms.

From these deformations, using standard tracking techniques, the propagation speed of the transverse wave front (6) is calculated.

From the speeds, the transverse or shear modulus of elasticity is obtained from the equation:

$$v = \sqrt{\frac{G}{\rho}} \quad \text{(Equation 8)}$$

G being the transverse or shear modulus of elasticity and p the density of the soft solid.

Finally, from the transverse elastic modulus obtained at different points of the soft solid, elastography images can be obtained that are used to make a medical diagnosis.

The invention claimed is:

1. A method for obtaining elastic properties of a soft solid on which an acoustic radiation force is exerted which causes deformations in said soft solid, wherein the method comprises the steps of:

applying a pulsed or amplitude-modulated signal to an ultrasound transducer, generating, in the ultrasound transducer, a focused vortex ultrasound beam, which generates a quasi-omnidirectional transverse wave front, characterized by a speed, which is transmitted through the soft solid, acquiring images of the soft solid while the wave front is propagated, making use of a second ultrasound transducer in contact with the soft solid, calculating the deformations produced in the soft solid by cross-correlation or Doppler techniques from the images, calculating the propagation speed of the wave front from the deformations, using standard tracking techniques, calculating the transverse modulus of elasticity (G) of the soft solid from the equation:

$$v = \sqrt{\frac{G}{\rho}}$$

wherein v is the propagation speed of the wave front and $\rho$ the density of the soft solid, and obtaining elastography images from the transverse modulus of elasticity at different points of the soft solid.

2. The method of claim 1, wherein the acoustic radiation force is given by a force field that is defined by:

$$F(x, y, z) = i\frac{\alpha(\omega)}{2\omega\rho_0 c_0}(P\nabla P^* - P^*\nabla P)$$

F being the force vector field, $\alpha(\omega)$ the absorption of the soft solid, w the angular frequency, $\rho_0$ the density of the soft solid, $c_0$ the speed of the wave front, P the pressure field produced, and P* the complex conjugate thereof.

3. The method of claim 1, wherein the ultrasound transducer is a single element transducer, comprising a holographic lens, positioned on the surface of the ultrasound transducer, the holographic lens modifying the phase of the wave front so that it is adjusted to that of a focused acoustic vortex, given by:

$$A(x_0,y_0)=\exp(-ik_0\sqrt{x_0^2+y_0^2+F^2})\exp(-im\,\tan^{-1}(y_0,x_0))$$

$A(x_0, y_0)$ being the phase along the surface of the ultrasound transducer given by $x_0$, $y_0$, $k_0=2\pi f/c_0$ the wave number, wherein f is the frequency and $c_0$ is the speed of sound in the soft solid, F is the focal length of the lens and m the topological charge of the vortex.

4. The method of claim 3, wherein the sign of the topological charge m is varied by modifying the phase of the wave front at the output of the primary transducer using the lens, which works with a positive topological charge m at a first frequency and with a negative topological charge m at a second frequency.

5. The method of claim 3, wherein the sign of the topological charge m is varied by using two ultrasound transducers positioned in the form of concentric rings wherein each one comprises a different lens with a different topological charge m, one being positive and the other negative, and alternating the emission between one ultrasound transducer and another.

6. The method of claim 1, wherein the ultrasound transducer is a flat multi-element transducer, comprising elements that are adjusted to an amplitude given by |A| and a phase given by $\tan^{-1}(\text{Im}(A)/\text{Re}(A))$, being:

$$A(x_0,y_0)=\exp(-ik_0\sqrt{x_0^2+y_0^2+F^2})\exp(-im\,\tan^{-1}(y_0,x_0))$$

$A(x_0, y_0)$ being the phase along the surface of the ultrasound transducer given by $x_0$, $y_0$ which represent the spatial position in Cartesian coordinates of each element of the primary transducer, $k_0=2\pi f/c_0$ the wave number, wherein f is the frequency and $c_0$ is the speed of sound in the soft solid, F is the focal length of the lens and m the topological charge of the vortex.

7. The method of claim 4, wherein the sign of the topological charge m is varied by angularly reversing the phase of the elements of the ultrasound transducer.

8. The method of claim 1, wherein the ultrasound transducer is a geometric focusing multi-element transducer, wherein each element of the ultrasound transducer is adjusted to an amplitude given by |A| and a phase given by $\tan^{-1}(\text{Im}(A)/\text{Re}(A))$, being:

$$A(x_0,y_0)=\exp(-im\,\tan^{-1}(x_0,y_0))$$

wherein $A(x_0, y_0)$ is the phase along the surface of the ultrasound transducer given by $x_0$, $y_0$ which represent the spatial position in Cartesian coordinates of each element of the primary transducer, and m the topological charge of the vortex.

9. The method of claim 8, wherein the sign of the topological charge m is varied by angularly reversing the phase of the elements of the ultrasound transducer.

* * * * *